United States Patent [19]

DeFazio et al.

[11] 4,447,545
[45] May 8, 1984

[54] BLADDER CANCER DETECTION

[75] Inventors: Sally R. DeFazio, Watertown; James J. Gozzo, Westwood; Anthony P. Monaco, Newton, all of Mass.

[73] Assignee: New England Deaconess Hospital, Boston, Mass.

[21] Appl. No.: 388,675

[22] Filed: Jun. 15, 1982

Related U.S. Application Data

[63] Continuation-in-part of Ser. No. 203,146, Nov. 3, 1980, abandoned.

[51] Int. Cl.³ .................... G01N 33/48; G01N 33/68
[52] U.S. Cl. ................................ 436/518; 436/542; 436/64; 436/86; 436/804; 436/811; 436/813; 436/815; 435/4; 435/7
[58] Field of Search .................... 424/1; 435/4, 7; 436/518–535, 63, 64, 86, 813, 504, 514–517, 536, 538–542, 804, 811, 815

[56] References Cited

U.S. PATENT DOCUMENTS

| 3,960,827 | 6/1927 | Bjorklund | 260/112 |
|---|---|---|---|
| 4,132,769 | 1/1979 | Osther | 424/1 |
| 4,184,849 | 1/1980 | Cambiaso et al. | 23/230 B |
| 4,269,765 | 5/1981 | Matsuda et al. | 260/112 B |

FOREIGN PATENT DOCUMENTS 53-7886015  7/1978  Japan .

OTHER PUBLICATIONS

Chromatography of Proteins, G. Bernardi, [29], pp. 225-339, Methods of Enzymology, vol. 22.
Hydroxyapatite, Bio-Rad Corp., catalogue, pp. 59-64.
Partial Purification of Carcinoembryonic-Reactive Antigen from Breast Neoplasm, etc., Santen et al., Cancer Research 40, 1181-1188, Apr., 1980.
Detection of Bladder Cancer-Associated Antigens in Urine by Micro-Complement Fixation, J. J. Gozzo et al., Surg. Forum 15:117-119, 1974.
Immunological Detection of Bladder Cancer Specific Antigen in Urine, J. J. Gozzo, et al., Fed. Proc. 33:805, 1974.
Immunological Detection of Human Bladder Carcinoma, A. P. Monaco, et al., Annals of Surgery, 182:325-333, 1975.
Immunological Detection and Partial Purification of Human Urinary Bladder Tumor Associated Antigens in Urine, W. Cronin et al., Fed. Proc. 34:1042, 1975.
Partial Purification and Characterization of Urine Components from Patients with Bladder Cancer, W. Cronin et al., Fed. Proc. 35:547, 1976.
Immunological Detection of Human Bladder Carcinoma, A. P. Monaco et al., Urology Digest, pp. 31-32, Apr., 1976.
Use of Heterogenous and Monospecific Antisera for the Diagnosis of Bladder Cancer, J. J. Gozzo et al., J. of Urology, 118:748-751, 1977.
Qualitative Analysis of Tumor Related Components in Bladder Cancer Urines, P. O'Brien et al., Fed. Proc. 36:1327, 1977.
Identification of Urinary Bladder Tumor Associated Antigens in Cancer Urine, W. Cronin et al., Fed. Proc. 36:1327, 1977.
Identification of Tumor Antigens in Urine of Patients with Bladder Cancer, W. Cronin et al., Fed. Proc. 37:1486, 1978.
Qualitative Analysis of Proteinuria Associated with Bladder Cancer, P. O'Brien et al., Invest. Urol., 17:28-32, 1979.
Acute Phase Reactant Proteins in the Clinical Management of Carcinoma of the Bladder, R. Bastable et al., British Journal of Urology, 51:283, 1979.
Reevaluation of C-Reactive Protein in Cancer Sera by Radioimmunoassay and Radial Diffusion, D. Drahovsky et al., Oncology 38:286, 1981.
Prognostic Significance of Serum Proteins in Invasive Bladder Cancer, J. O'Quigley et al., Eur. J. Cancer 17:251, 1981.
Bastable, R. B. et al., J. Urology, vol. 51, pp. 283-289 (1979).
Siboo, R. et al., J. Immunological Methods, vol. 23, pp. 59-67 (1978).

Primary Examiner—Benjamin R. Padgett
Assistant Examiner—M. Moskowitz
Attorney, Agent, or Firm—Lahive & Cockfield

[57] ABSTRACT

Disclosed is a technique for screening populations to detect potential bladder cancer patients. The screening test is based on a discovered correlation between the respective ratios of C-reactive protein to total protein in urine and serum and the incidence of bladder cancer.

10 Claims, 1 Drawing Figure

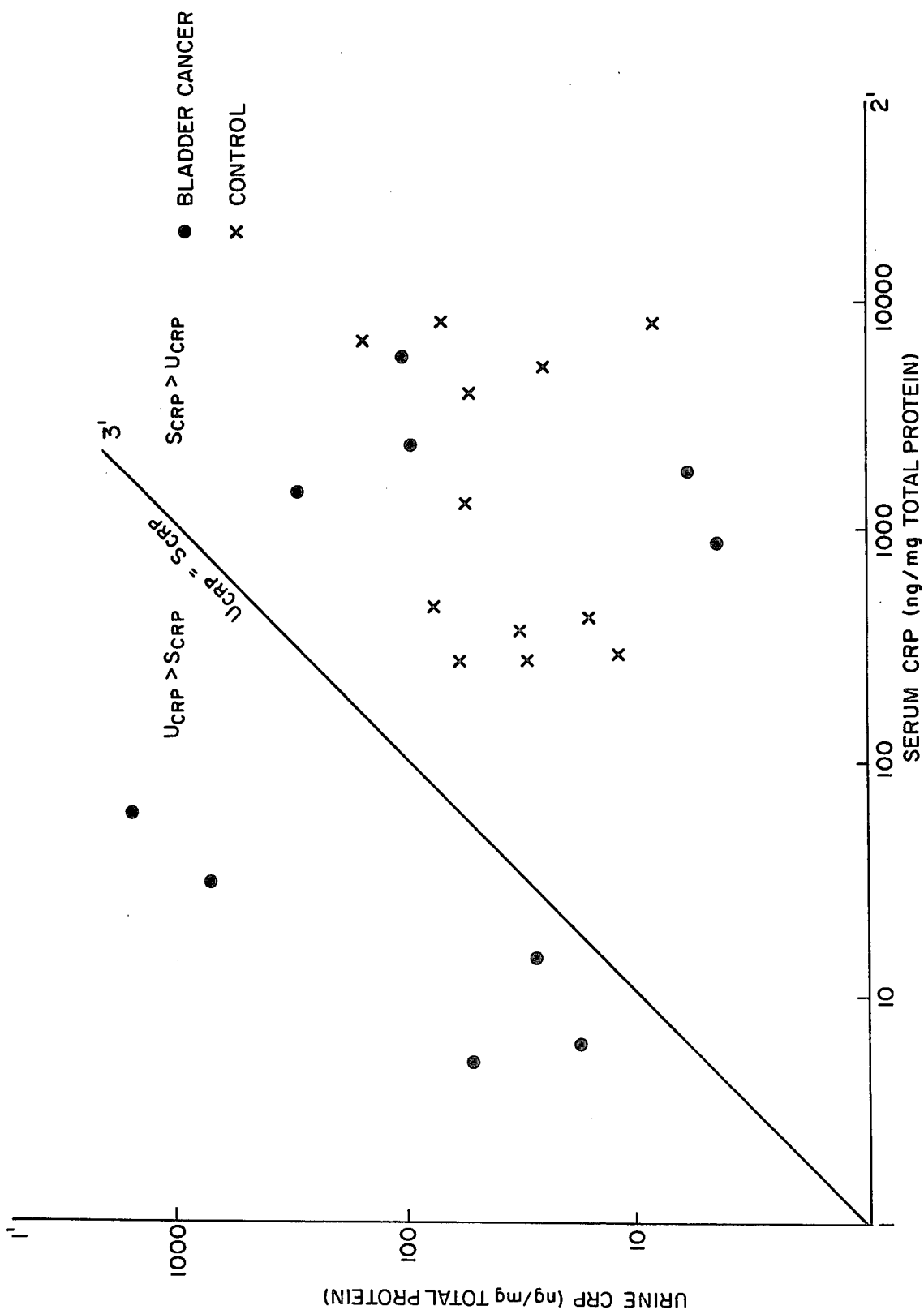

BLADDER CANCER DETECTION

The Government has rights in this invention pursuant to National Institute of Health Grant CA 20888, awarded to New England Deaconess Hospital by the Department of Health and Human Services.

REFERENCE TO RELATED APPLICATION

This application is a continuation-in-part of copending U.S. application Ser. No. 203,146, filed Nov. 3, 1980, now abandoned entitled "Bladder Cancer Detection", the disclosure of which is incorporated herein by reference.

BACKGROUND OF THE INVENTION

This invention relates to a method of detecting the presence of bladder cancer in humans. More particularly, it relates to the discovery that if the ratio of C-reactive protein ("CRP") to total protein in urine is higher than the ratio of CRP to total protein in serum, this is indicative of bladder cancer and to a method for making this determination.

Bladder cancer ranks eleventh in cancer deaths in the United States. In general, the five year survival rate for people with low grade tumors is greater than 60 percent, while the five year survival rate for people with high grade and often metastatic tumors is less than 15 percent. Currently, the diagnosis and management of bladder cancer patients involves utilization of methods such as cystoscopy, urinary cytology, and the quantitation of normal and abnormal plasma related components in urine. Repeated cystoscopy involves patient discomfort, is costly, and may expose patients to certain surgical risks. Normal serum and plasma related components appear to have limited usefullness in the early diagnosis of bladder cancer as many of these same components are also present in increased concentrations in urine from patients with non-neoplastic disease.

The discovery of a substance in the urine of patients afflicted with bladder cancer which was associated with the cancer and indicative of its presence could provide a basis for a diagnostic test for the presence of bladder cancer. The development of a reliable and sensitive assay capable of detecting the presence of such a substance in urine would have many advantages over current methods of detecting bladder neoplasms. Since such a test would be non-invasive, it could be routinely employed to test urine from groups of high risk individuals such as those with occupational exposures to certain bladder carcinogens and other high risk groups. To verify the initial diagnosis of potential bladder cancer, further tests could be conducted.

Significant progress in the effort to detect and isolate such a tumor specific protein fraction has been made in the last ten years. Publications of interest in this area include: *Detection of Bladder Cancer-Associated Antigens in Urine by Micro-Complement Fixation*, J. J. Gozzo et al., Surg. Forum 25:117–119, 1974; *Immunological Detection of Bladder Cancer Specific Antigen in Urine*, J. J. Gozzo et al., Fed. Proc. 33:805, 1974; *Immunological Detection of Human Bladder Carcinoma*, A. P. Monaco et al., Annals of Surgery, 182:325-333, 1975; *Immunological Detection and Partial Purification of Human Urinary Bladder Tumor Associated Antigens in Urine*, W. Cronin et al., Fed. Proc. 34:1042, 1975; *Partial Purification and Characterization of Urine Components from Patients with Bladder Cancer*, W. Cronin et. al., Fed. Proc. 35:547, 1976; *Immunological Detection of Human Bladder Carcinoma*, A. P. Monaco et. al., Urology Digest, pages 31–32, April, 1976; *Use of Heterogenous and Monospecific Antisera for the Diagnosis of Bladder Cancer*, J. J. Gozzo et al., J. of Urology, 118:748-751, 1977; *Qualitative Analysis of Tumor Related Components in Bladder Cancer Urines*, P. O'Brien et al., Fed. Proc. 36:1327, 1977; *Identification of Urinary Bladder Tumor Associated Antigens in Cancer Urine*, W. Cronin et al., Fec. Proc. 36:1327, 1977; *Identification of Tumor Antigens in Urine of Patients with Bladder Cancer*, W. Cronin et al., Fed. Proc. 37:1486, 1978; *Qualitative Analysis of Proteinuria Associated with Bladder Cancer*, P. O'Brien et al., Invest. Urol., 17:28–32, 1979. This literature suggests that bladder cancer is associated with a number of nonspecific responses which are reflected in an elevation of normal protein components in the plasma or urine of cancer patients. Because these same components are also increased in other nonmalignant diseases, their use as tumor markers is not normally suitable. However, this literature also presents strong evidence that bladder tumor associated antigens do exist, and that it is possible that detection of such tumor associated antigens may be useful in the diagnosis of bladder cancer.

CRP is normally present in serum in low concentrations but elevated levels of CRP in serum are associated with certain diseases involving inflammation or tissue damage. As discussed in *Acute Phase Reactants in Cancer*, E. H. Cooper et al, Adv. Cancer Res., 30:1–44 (1979), various cancers can cause elevated CRP in serum. However, Mukin et al, in *Determination of C-reactive Protein in the Urine of Patients with Pyretic Proteinuria*, Zdravookhr Byeloruss, 7:23–24 (1966), found that unless patients are somewhat proteinuric, they do not excrete CRP in the urine even if the serum levels are elevated. No other studies have been reported where elevated urine CRP levels have measured and correlated with serum CRP levels.

Immunoassays involving tagged antibodies specific to various materials which behave as antigens in vivo are now widely available. The broad approach of these assays is to incubate a test sample suspected to contain the antigen with "tagged" antibody under conditions such that the detection of the antibody in the test vessel after incubation, as evidenced by detection of the tag, implies the presence of antigen in the sample. An immunoassay has now been developed for detection of CRP in urine and serum. Such an assay is a non-invasive, reliable screening test for bladder cancer detection. Since the first stage of detection proceeds by urinalysis, screening of at risk populations is practical. In view of the marked difference in survival rate in patients between early and late diagnosis of bladder cancer, the importance of such a development is manifest.

SUMMARY OF THE INVENTION

The instant invention provides a simple method for detection of bladder cancer. The invention also provides means by which at risk populations can be screened for early stage bladder cancer.

In one aspect of the invention, broad based screening of at risk populations for bladder cancer can be achieved by testing for the presence of CRP in urine samples. While some inflammatory diseases other than bladder cancer cause elevated urinary CRP levels, the ratio of CRP to total urine protein in patients having bladder cancer is generally higher than the CRP/total urine protein ratio in non-bladder cancer patients. In another aspect of the invention, the ratio of CRP to total protein in urine is compared with the ratio of CRP to total protein in serum. When the urine ratio equals or exceeds the serum ratio, the urine level cannot be from spillover from the serum and bladder cancer is indicated.

Immunoassay techniques may be utilized to detect the CRP levels. Antibody to CRP may be tagged by known methods with a moiety detectable by chemical methods such as an enzyme or a fluorescent molecule, with a radioactive atom, or with a biotin-avidin-enzyme (e.g., horseradish peroxidase) conjugate. The tagged antibodies are extremely useful tools for the detection of bladder cancer.

The analysis of the invention can use any one of the conventional immunoassay methods for detection of the presence of CRP. For example, a sandwich technique wherein, during the course of a positive test, a "sandwich" of antibody-antigen-tagged antibody is built up may be employed. In a first step, a urine sample is incubated with immobilized antibody so that tumor associated CRP, if present in the urine, is coupled to the immobilized antibody by an antigen-antibody bond. After thorough washing, the support is again incubated, this time with an antibody coupled with a detectable moiety such as an enzyme, so that the coupled antibody will bind with tumor associated CRP if present on the support. The support is then assayed for the detectable moiety, and the results are compared with a standard such as a standard curve. The level of total protein in the urine is determined by conventional means and a ratio of CRP to total protein in urine is determined. Using the same technique, except substituting a serum sample for the urine sample, the ratio of CRP to total protein in serum is determined. A comparison of the two ratios is used as the indicator of a bladder carcinoma.

Accordingly, it is an object of the invention to provide a simple procedure for detection of the presence of a bladder cancer in a patient.

Another object of the invention is to provide a screening procedure whereby at risk populations can be tested for potential bladder cancer.

BRIEF DESCRIPTION OF THE DRAWING

The single FIGURE of the drawing illustrates a comparison of CRP/total protein levels in urine and serum for bladder cancer and non-bladder cancer patients.

DESCRIPTION OF A PARTICULAR EMBODIMENT

Collection of bladder cancer associated antigens from urine from bladder cancer patients ("cancerous urine") is difficult in that many proteins present in normal urine are apparently present in cancerous urine in various stages of denaturation or aggregation. However, as is disclosed in copending U.S. patent application Ser. No. 203,146 (the "'146 application") hydroxyapatite is a material uniquely suited for the fractionation of bladder cancer associated proteins from the other myriad protein species. The '146 application disclosed a hydroxyapatite separation technique whereby two distinct protein fractions, designated protein A and protein B, could be eluted from the hydroxyapatite at elevated phosphate levels. The '146 application also disclosed antibody production and assay methods for the two bladder cancer associated proteins. Using commercially available anti-CRP, purchased from Miles Laboratories, in an immunoelectrophoresis test, run at pH 8.2 in agarose, protein B was determined to be heterogeneous and to include as one of its components CRP. CRP is a protein commonly found in low levels in normal serum and in higher levels in some inflammatory diseases including metastastic cancers. A detection test for bladder cancer has been developed utilizing comparative assays for CRP/total protein levels in urine and serum.

The present invention comprises both a screening test of at risk populations for bladder cancer and a detection method for bladder cancer. As a screening test, the assay procedures described herein may be used to determine the presence of CRP in urine. It has been determined that approximately 61% of urine samples from patients with bladder cancer were positive for CRP while only about 24% of control samples (including normal individuals, patients with other malignancies, patients with non-malignant urogenital disease and various other conditions with associated proteinuria) were positive. All patients tested who were truly healthy were negative for urinary CRP. By screening a population of likely bladder cancer patients for the presence of CRP in urine, one can determine whether further testing for bladder cancer is warranted.

The detection test of the present invention is based on the discovery that the ratio of CRP to total urinary protein is greater in bladder cancer patients than the ratio of CRP to total protein in serum. While previous investigators have attempted to use serum levels of CRP to detect bladder cancer, serum tests cannot be used for early detection because the level of CRP is not elevated in serum in early stages of bladder cancer.

The single FIGURE of the drawing illustrates the results of an experiment using the assay procedures described herein. Vertical axis 1-1' represents the measured CRP/total protein ratio in urine, while horizontal axis 1-2' represents the CRP/total protein level in serum. Diagonal line 1-3' represents the situation where CRP/total protein ratios for urine and serum is equal. As is illustrated, 50% of the bladder cancer patients had CRP/total urine protein ratios greater than CRP/total serum protein ratios while none of the non-bladder cancer patients had the CRP/total urine protein ratio greater than their CRP/total serum protein ratio. The false positive result (CRP/total urine protein>CRP/total serum protein) in non-bladder cancer patients has been negligible. If the level of CRP in serum is approximately normal and CRP is found in the urine, the chances are even greater that the patient has bladder cancer. Since early stage bladder cancer does not normally elevate serum CRP levels, the test can be used to detect bladder cancer at early stages. Because the possibility of arresting bladder cancer is greater if detected at early stages, this test has great utility.

A number of different assays may be used to detect levels of CRP in urine and serum. Complement fixation may be used as a simple screening test for CRP in urine. In the complement fixation test, if a 50% fixation level is not reached when the total protein concentration reaches 250 $\mu$g/ml, the test is considered negative. It has also been discovered that if the complement fixation reaches the 50% point at lower protein concentrations, there is a greater chance that bladder cancer is present. Immunoelectrophoresis can also be used as a qualitative detection method.

For determination of actual levels of CRP, the use of quantitative immunoassays is indicated. These immunoassays include radioimmunoassays, chemical immunoassays and enzyme immunoassays. In these assays, a detectable moiety is attached to a protein, either CRP or anti-CRP, by conventional methods such as chemical conjugation or chloramine T chemical addition. In a preferred embodiment, anti-CRP may be used as a carrier of the detectable moiety in a variation of the sandwich technique wherein anti-CRP is adsorbed on an insoluble support, a sample suspected of containing bladder cancer associated CRP is allowed to react with the immobilized antibody, and the presence of bound protein is detected with labelled antibody. For example, the N-hydroxysuccinimide ester of biotin can be added to purified antisera to produce antibody-biotin conjugates. These in turn can be detected with a commercially available reagent comprising a conjugate of avidin, an egg-white protein having a high and specific affinity for biotin, and an enzyme such as horseradish peroxidase (HRP). Addition of the avidin-HRP conjugate, a washing step, and a subsequent addition of a substrate solution for the HRP results in a detectable color change in the test well if antigen were present in the test sample. This test can be run with either urine or serum to detect CRP.

The invention will be further understood from the following nonlimiting exemplary material.

ASSAY PROCEDURE

Purified anti-CRP produced as disclosed in the '146 application or purchased commercially from a source such as Miles Laboratories is introduced into the wells of a microcuvette plate (Cuvette-Pak, Gilford Instrument Laboratories, Inc.) at a concentration of about 0.01 mg/ml in phosphate buffered saline having a pH of 7.2 (0.2 ml/well). The antibody is incubated in the wells for eighteen hours at 4° C. to immobilize the antibody directly onto the test well surfaces. Each well is then washed ten times with phosphate buffered saline (pH=7.2) containing 0.05% anionic surfactant (TWEEN 20). This wash step is repeated after each incubation to minimize nonspecific adsorptions. Samples to be tested are then added to the respective test wells and incubated for one hour at room temperature. Samples taken from a patient afflicted with bladder cancer will contain CRP and thus when tested will result in the formation of an antigen-antibody bond with the immobilized antibody in the wells.

Separately, a second portion of the antibody is added to a ten-fold molar excess of the N-hydroxysuccinimide ester of biotin. This material is dissolved in a minimum volume of dimethyl formamide and incubated with the antibody for one hour. After dialysis against pH=7.2 buffered saline to remove unbound biotin, an antibody-biotin conjugate is produced.

After washing the wells, sufficient biotin labelled antisera, in phosphate buffered saline (PBS), at a concentration in the range of 0.01 mg/ml (approximately equal to the amount of antibody originally adsorbed in the test wells) is added to each of the wells and incubated for one hour at room temperature. There is produced in any well that had been incubated with the sample containing CRP a "sandwich" comprising antibody immobilized on the well, antigen, and biotin-labelled antibody. After repeated washings with PBS-TWEEN solution, wells which contain the antigen and therefore the tagged antibody are found to contain biotin.

Next, a conjugate of avidin and horseradish peroxidase in phosphate buffered saline (1:4500, Vector Labs) is added to the test wells and incubated at room temperature for one hour. During this time, avidin binds with any biotin in the well. After repeated washings, those wells which contain biotin will contain horseradish peroxidase.

Next, a substrate solution which undergoes a color change in the presence of horseradish peroxidase is added to the wells. Thus, for example, a 10 ml solution consisting of 1.0 mg of 4-amino-antipyrine, 500 mg of phenol, and 1 $\mu$l of 30% $H_2O_2$ in one liter of 0.2 M phosphate buffer, pH 6.0, is prepared. This substrate solution is added to each well (at approximately 0.25 ml/well) and incubated for 20 minutes, at which time 10 microliters of 3 M sodium thiocyanate is added to each well to inhibit further development of color. Optical absorbance measurements with a spectrophotometer or any one of several commercially available instruments capable of reading optical density directly in microtiter wells gives a readout of the color intensity of each of the plates. The presence of color above a baseline level implies that the sample contains CRP. Using a standard curve, one can determine the concentration of CRP in the sample.

The sample may consist of either urine or serum. In either case, the CRP level can be measured in this manner. The protein concentrations of the urine and serum can be detected using conventional methods such as a Lowrey assay or any other assay for total protein. Using the results of these tests, the CRP/total protein levels for urine and serum can be determined and compared.

If the urine shows a detectable CRP level, the patient should be further tested for potential bladder cancer. If the CRP/total protein level in urine is greater than the CRP/total protein level in serum, bladder cancer is indicated. If the CRP/total protein level in serum is normal (less than 10 $\mu$g/ml) and there is detectable CRP in the urine, bladder cancer is highly likely.

The invention may be embodied in other specific forms without departing from the spirit and scope thereof. Accordingly, other embodiments are within the following claims.

What is claimed is:

1. A method for screening a patient for the presence of a bladder carcinoma, said method comprising the steps of:
    (A) assaying for the ratio of C-reactive protein to total protein in a sample of the urine of said patient;
    (B) assaying for the ratio of C-reactive protein to total protein in a sample of the serum of said patient; and
    (C) comparing the ratio determined by assay in step A to the ratio determined by assay in step B, whereby
        (i) a finding of the absence of C-reactive protein in said urine sample is indicative of the absence of a bladder carcinoma; and
        (ii) a finding that the ratio determined in step A is greater than the ratio determined in step B is indicative of the presence of a bladder carcinoma.

2. The method of claim 1 wherein the ratios determined in steps A and B are determined by a method comprising the steps of:
    (1) testing the sample to determine the total protein concentration;
    (2) assaying the sample to determine the C-reactive protein concentration; and (3) dividing the results of step 2 by the results of step 1.

3. The method of claim 2 wherein the assaying of the sample comprises an assay from a group consisting of radioimmunoassays, chemical immunoassays, and enzyme immunoassays.

4. The method of claim 3 wherein the assaying of the sample is conducted by a process comprising the steps of:
   (a) incubating a portion of said sample with an antibody complementary to C-reactive protein immobilized on an insoluble support under conditions to form an antigen-antibody bond between said immobilized antibody and said C-reactive protein;
   (b) washing the insoluble support to remove unbound components from the reactive system of step a;
   (c) incubating the support resulting from step b with a reagent comprising said antibody tagged with a detectable moiety under conditions to form an antigen-antibody bond between said tagged antibody and said C-reactive protein bound to said insoluble support;
   (d) washing the insoluble support to remove unbound components from the reaction system of step c;
   (e) assaying the support resulting from step d for the presence of said detectable moiety; and
   (f) comparing the results of the assay of step e to a standard.

5. The process of claim 4 wherein said detectable moiety is a moiety detectable by chemical means.

6. The process of claim 4 wherein said detectable moiety includes a radioactive atom.

7. The process of claim 4 wherein said detectable moiety is a moiety having a high binding affinity for an enzyme conjugate.

8. The process of claim 7 wherein said moiety is biotin.

9. The process of claim 4 wherein said detectable moiety comprises an enzyme.

10. The process of claim 4 wherein said standard comprises a standard curve.

* * * * *